United States Patent [19]

Scates et al.

[11] Patent Number: 5,155,265
[45] Date of Patent: Oct. 13, 1992

[54] PURIFICATION OF ACETIC ACID WITH OZONE FOLLOWED BY TREATMENT WITH ACTIVATED CARBON AND/OR AN ION-EXCHANGE RESIN

[75] Inventors: Mark O. Scates, Pearland; Russell K. Gibbs, Jr., Houston; G. Paull Torrence, Corpus Christi, all of Tex.

[73] Assignee: Hoechst Celanese Corporation, Somerville, N.J.

[21] Appl. No.: 687,098

[22] Filed: Apr. 19, 1991

Related U.S. Application Data

[63] Continuation of Ser. No. 447,412, Dec. 7, 1989, abandoned, which is a continuation-in-part of Ser. No. 137,844, Dec. 23, 1987, abandoned.

[51] Int. Cl.$^5$ ............... C07C 51/47; C07C 51/487; C07C 51/50; C07C 53/08
[52] U.S. Cl. .................... 562/608; 562/519
[58] Field of Search .................. 562/608, 607, 519

[56] References Cited

U.S. PATENT DOCUMENTS

| | | | |
|---|---|---|---|
| 3,928,434 | 12/1975 | Saunby | 562/608 |
| 4,615,806 | 10/1986 | Hilton | 562/608 X |
| 4,664,753 | 5/1987 | Erpenbach et al. | 562/608 |
| 4,894,477 | 1/1990 | Scates et al. | 562/608 X |
| 5,001,259 | 3/1991 | Smith et al. | 562/607 X |

Primary Examiner—Vivian Garner
Attorney, Agent, or Firm—Depaoli & O'Brien

[57] ABSTRACT

Acetic acid containing iodide, unsaturates and carbonyl impurities is purified by treatment with ozone and thereafter contacted with activated carbon and/or an ion-exchange resin for removal of impurities.

4 Claims, No Drawings

PURIFICATION OF ACETIC ACID WITH OZONE FOLLOWED BY TREATMENT WITH ACTIVATED CARBON AND/OR AN ION-EXCHANGE RESIN

CROSS REFERENCE TO RELATED APPLICATIONS

This application is a continuation of application Ser. No. 07/447,412, filed Dec. 7, 1989, now abandoned, which is a continuation-in-part of Application Ser. No. 137,844, filed Dec. 23, 1987, now abandoned.

Application Ser. No. 936,188, filed Dec. 1, 1986 (now abandoned), discloses purification of acetic acid by treatment with a compound such as hydrazine or derivatives thereof.

BACKGROUND OF THE INVENTION

1. Field of the Invention

This invention relates to the purification of acetic acid and relates more particularly to the purification of acetic acid resulting from the catalytic carbonylation of methanol.

2. Description of the Prior Art

Various methods have been employed for producing acetic acid including, for example, the oxidation of acetaldehyde, the oxidation of petroleum naphtha, butane or the like, or the direct synthesis from methanol and carbon monoxide. One of the more useful commercial methods for the production of acetic acid is the carbonylation of methanol as disclosed in U.S. Pat. No. 3,769,329. The carbonylation catalyst comprises rhodium, either dissolved or otherwise dispersed in a liquid reaction medium or else supported on an inert solid, along with a halogen-containing catalyst promoter as exemplified by methyl iodide. The rhodium can be introduced into the reaction system in any of many forms, and it is not relevant, if indeed it is possible, to identify the exact nature of the rhodium moiety within the active catalyst complex. Likewise, the nature of the halide promoter is not critical. A large number of suitable promoters are disclosed, most of which are organic iodides. Typically, the reaction is conducted with the catalyst being dissolved in a liquid reaction medium through which carbon monoxide gas is continuously bubbled.

An improvement in the prior art process for the carbonylation of an alcohol to produce the carboxylic acid having one carbon atom more than the alcohol in the presence of a rhodium catalyst is disclosed in copending, commonly assigned application U.S. Ser. No. 699,525, filed Feb. 8, 1985, now abandoned and European patent application Ser. No. 161,874, published Nov. 21, 1985. As disclosed therein, acetic acid (HAc) is produced from methanol (MeOH) in a reaction medium comprising methyl acetate (MeOAc), methyl halide, especially methyl iodide (MeI), and rhodium present in a catalytically-effective concentration. The invention therein resides primarily in the discovery that catalyst stability and the productivity of the carbonylation reactor can be maintained at surprisingly high levels, even at very low water concentrations, i.e., 4 wt. % or less, in the reaction medium (despite the general industrial practice of maintaining approximately 14 wt. % or 15 wt. % water) by maintaining in the reaction medium, along with a catalytically-effective amount of rhodium, at least a finite concentration of water, methyl acetate and methyl iodide, a specified concentration of iodide ions over and above the iodide content which is present as methyl iodide or other organic iodide. The iodide ion is present as a simple salt, with lithium iodide being preferred. The applications teach that the concentration of methyl acetate and iodide salts are significant parameters in affecting the rate of carbonylation of methanol to produce acetic acid especially at low reactor water concentrations. By using relatively high concentrations of the methyl acetate and iodide salt, one obtains a surprising degree of catalyst stability and reactor productivity even when the liquid reaction medium contains water in concentrations as low as about 0.1 wt. %, so low that it can broadly be defined, simply as "a finite concentration" of water. Furthermore, the reaction medium employed improves the stability of the rhodium catalyst, i.e., resistance to catalyst precipitation, especially during the product-recovery steps of the process wherein distillation for the purpose of recovering the acetic acid product tends to remove from the catalyst the carbon monoxide which in the environment maintained in the reaction vessel, is a ligand with stabilizing effect on the rhodium. U.S. Ser. No. 699,525 is herein incorporated by reference.

The acetic acid which is formed by the carbonylation of methanol is converted to a high purity product by conventional means such as by a series of distillations. While it is possible in this manner to obtain acetic acid of relatively high purity, the acetic acid product contains a considerable amount of by-product impurities, determinable on the basis of their reducing action on permanganate. The amount of such reducing impurities is referred to as the permanganate time. Since the permanganate time is an important commercial test which the acid product must meet for many uses, the presence therein of such impurities is highly objectionable. Apparently, the removal of minute quantities of these impurities by conventional rectification alone is difficult since the impurities distill over with the acetic acid.

Among the residual impurities which have been found to degrade the permanganate time are alkyl iodide impurities which are most likely carried over into the product stream from the catalyst solution in the reactor. Also found in the acetic acid product are various unsaturated and carbonyl impurities including crotonaldehyde, ethyl crotonaldehyde and the 2-methyl-2-pentanal isomer thereof. As has been previously stated, it is both difficult and costly to remove the iodides, unsaturates and carbonyl impurities from the acetic acid product by physical methods since such impurities are present in such minute amounts. Accordingly, an economical process for removing such impurities is needed.

Various methods have been suggested to purify or remove nonacidic components from carboxylic acids. For example, U.S. Pat. No. 4,576,683 discloses a method of separating $C_1$-$C_{10}$ aliphatic and $C_3$-$C_{10}$ olefinic carboxylic acids from mixtures with nonacids by extractive distillation using an amide as an extractant to recover an extractant-acid mixture by rectification. The method disclosed in the patent is described as being particularly suitably applied on aqueous mixtures of formic, acetic and/or propionic acid which mixtures contain unconverted hydrocarbons and other oxygenated compounds such as mixtures with alcohols, aldehydes and/or ketones and which may also contain further contaminants such as effluents from the oxidation reactions. The amide extractants utilized in the patent are selected from lactams having 5 or 6 membered rings.

Pyrrolidone and derivatives thereof are specifically disclosed.

U.S. Pat. No. 4,268,362 is concerned with providing a method of removing formaldehyde from raw acetic acid which has been formed by synthetic reactions such as oxidation of acetaldehyde, gas phase or liquid phase oxidation of butane, oxidation of petroleum naphtha or paraffins, as well as the reaction of methanol with carbon monoxide. The separation process involves treating the acetic acid in a heating zone at a temperature at about the boiling point of the acetic acid or higher, removing the heated product and delivering it to a distillation zone and operating the distillation zone so as to obtain a lower boiling fraction, a higher boiling fraction and an intermediate acetic acid fraction which will have a formaldehyde content of 300 ppm or lower.

U.S. Pat. No. 3,725,208 is concerned with a process for the removal of small amounts of aldehyde impurities from acrylic acids which comprises adding to the acrylic acid minor amounts of a compound selected from the group consisting of sulfuric acid, hydrazine, phenyl hydrazine, aniline, monoethanolamine, ethylene diamine and gylcine and subjecting the acrylic acid mixture to distillation. Although hydrazine usually reacts exothermically with acrylic acid to form pyrrazolidone, and amines such as monoethanolamine and ethylene diamine have the properties of forming salts and aminocarboxylic acids with acrylic acid, the patentee states that it was surprising that these compounds react predominantly with aldehydes contained in acrylic acid and can remove them from the acrylic acid.

Japanese patent application Ser. No. 60-222439 discloses purification of acetic anhydride produced by the ketene process in which acetic acid is thermally cracked to ketene which then combines with acetic acid through an absorption reaction to produce acetic anhydride. The impurities contained in acetic anhydride produced in this manner are many low and high boiling compounds present at the time when acetic acid is thermally cracked and when acetic acid and ketene are reacted. However, the exact nature of the impurities contained in the acetic anhydride are not disclosed. Treatment with ozone gas in the absence of an oxidation catalyst was found to provide a quality product equal to or greater than that produced in purification by distillation.

Japanese Patent Publication 55(1980)-64545, published May 15, 1980, discloses purification of acetic acid in which an ozone-containing gas is introduced to the acetic acid in the absence of an oxidation catalyst to obtain acetic acid of a higher quality as measured by a potassium permanganate test and sulfuric acid color test. The identities of the impurities contained in acetic acid are not identified.

U.S. Pat. No. 3,928,434 to Saunby discloses reducing the content of oxidizable impurities in acetic acid produced by hydrocarbon oxidation by treating the acetic acid with oxygen in the presence of a transition metal compound to oxidize unsaturated ketones. Saunby, in col. 1, lines 45-60, points out that, heretofore, oxidizable impurities can be destroyed by reaction with ozone, but that such treatment suffers the drawback of the risk involved in handling ozone at elevated temperatures in organic liquid. The Saunby disclosure is directed to removal of alpha, beta-unsaturated ketone impurities in acetic acid produced by hydrocarbon oxidation.

SUMMARY OF THE INVENTION

The present invention is directed to the purification of acetic acid and the improvement of permanganate time by subjecting the acid to treatment with ozone or an ozone containing gas and thereafter contacting the acetic acid with activated carbon and/or an ion-exchange resin for removal of iodides, unsaturates and carbonyl impurities. Thus acetic acid, such as formed and recovered from the catalytic carbonylation of methanol, can be purified of minute amounts of unsaturates, iodides and carbonyl compounds by catalytic treatment with ozone which reacts with such impurities. In a further embodiment, the ozone-derived impurities are subsequently separated from the acetic acid by adsorption on an absorbent such as activated carbon and/or an ion-exchange resin which is at least partially converted to the silver or mercury form.

DETAILED DESCRIPTION OF THE INVENTION

The ozonolysis treatment of the present invention is applicable to the purification of acetic acid which has been produced by the carbonylation of methanol in the presence of a metal catalyst such as rhodium. The purification process of the present invention is particularly useful when the carbonylation reaction is catalyzed by a metal such as rhodium and a halide promoter such as an organic halide disclosed in U.S. Pat. No. 3,769,329 to Paulik et al. The process of purifying acetic acid in the present invention is more particularly useful when the acetic acid is formed by the carbonylation of methanol under low water conditions such as set out in U.S. Ser. No. 699,525 wherein the catalyst solution not only contains the rhodium catalyst and organic halide promoter, but also contains an additional iodide salt. It has been found that organic iodide impurities as well as unsaturated and carbonyl impurities degrade the commercial value of the acetic acid product.

In the low water carbonylation of methanol to acetic acid as exemplified in U.S. Ser. No. 699,525, the catalyst which is employed includes a rhodium component and a halogen promoter in which the halogen is either bromine or iodine. Generally, the rhodium component of the catalyst system is believed to be present in the form of a coordination compound of rhodium with a halogen component providing at least one of the ligands of such coordination compound. In addition to the coordination of rhodium and halogen, it is also believed that carbon monoxide ligands form coordination compounds or complexes with rhodium. The rhodium component of the catalyst system may be provided by introducing into the reaction zone rhodium in the form of rhodium metal, rhodium salts and oxides, organic rhodium compounds, coordination compounds of rhodium, and the like.

The halogen promoting component of the catalyst system consists of a halogen compound comprising an organic halide. Thus, alkyl, aryl, and substituted alkyl or aryl halides can be used. Preferably, the halide promoter is present in the form of an alkyl halide in which the alkyl radical corresponds to the alkyl radical of the feed alcohol which is carbonylated. For example, in the carbonylation of methanol to acetic acid, the halide promoter will comprise methyl halide, and more preferably methyl iodide.

The liquid reaction medium employed may include any solvent compatible with the catalyst system and may include pure alcohols, or mixtures of the alcohol feedstock and/or the desired carboxylic acid and/or esters of these two compounds. The preferred solvent and liquid reaction medium for the low water carbonylation process comprises the carboxylic acid product. Thus, in the carbonylation of methanol to acetic acid, the preferred solvent is acetic acid.

Water is also added to the reaction medium but at concentrations well below what has heretofore been thought practical for achieving sufficient reaction rates. It is known that in rhodium-catalyzed carbonylation reactions of the type set forth in this invention, the addition of water exerts a beneficial effect upon the reaction rate, U.S. Pat. No. 3,769,329 to Paulik. Thus, commercial operations run at water concentrations of at least 14 wt. %. Accordingly, it is quite unexpected that reaction rates substantially equal to and above reaction rates obtained with such high levels of water concentration can be achieved with water concentrations below 14 wt. % and as low as 4.0 wt. % to 0.1 wt. %.

In accordance with the carbonylation process most useful in the present invention, the desired reaction rates are obtained even at low water concentrations by including in the reaction medium an ester which corresponds to the alcohol being carbonylated and the acid product of the carbonylation reaction and an additional iodide ion which is over and above the iodide which is present as a catalyst promoter such as methyl iodide or other organic iodide. Thus, in the carbonylation of methanol to acetic acid, the ester is methyl acetate and the additional iodide promoter is an iodide salt, with lithium iodide being preferred. It has been found that under low water concentrations, methyl acetate and lithium iodide act as rate promoters and catalyst stabilizers only when relatively high concentrations of 5 wt. % to 20 wt. % of each of these components are present and that the promotion is higher when both of these components are present simultaneously. This has not been recognized in the prior art previous to disclosure of commonly assigned U.S. Ser. No. 699,525. The concentration of lithium iodide used in the reaction medium of the preferred carbonylation reaction system is believed to be quite high as compared with what little prior art there is dealing with the use of halide salts in reaction systems of this sort.

The carbonylation reaction may be carried out by intimately contacting the feed alcohol, which is in the liquid phase, with gaseous carbon monoxide bubbled through a liquid reaction medium containing the rhodium catalyst, halogen-containing promoting component, alkyl ester, and additional soluble iodide salt promoter, at conditions of temperature and pressure suitable to form the carbonylation product. Thus, when the feed is methanol, the halogen-containing promoting component will comprise methyl iodide and the alkyl ester will comprise methyl acetate. It will be generally recognized that it is the concentration of iodide ion in the catalyst system that is important and not the cation associated with the iodide, and that at a given molar concentration of iodide, the nature of the cation is not as significant as the effect of the iodide concentration. Any metal iodide salt, or any iodide salt of any organic cation, can be used provided that the salt is sufficiently soluble in the reaction medium to provide the desired level of the iodide. The iodide salt can be a quaternary salt of an organic cation or the iodide salt of an inorganic cation. Preferably, it is an iodide salt of a member of the group consisting of the metals of Group Ia and Group IIa of the Periodic Table as set forth in the "Handbook of Chemistry and Physics" published by CRC Press, Cleveland, Ohio, 1975-76 (56th Edition). In particular, alkali metal iodides are useful, with lithium iodide being preferred. In the low water carbonylation most useful in this invention, the additional iodide over and above the organic iodide promoter is present in the catalyst solution in amounts of from 2-20, preferably 10-20 wt. %, the methyl acetate is present in amounts of from 0.5-30, preferably 2-5 wt. %, and the methyl iodide is present in amounts of from 5-20 and 14-16 wt.%. The rhodium catalyst is present in amounts of from 200-1,000 and preferably 300-600 ppm.

Typical reaction temperatures for carbonylation will be approximately 150°-250° C., with the temperature range of about 180°-220° C. being the preferred range. The carbon monoxide partial pressure in the reactor can vary widely but is typically about 2-30 atmospheres and preferably about 4-15 atmospheres. Because of the partial pressure of by-products and the vapor pressure of the contained liquids, the total reactor pressure will range from about 15-40 atmospheres.

A reaction and acetic acid recovery system which can be employed, within which the present improvement is used, comprises (a) a liquid-phase carbonylation reactor, (b) a so-called "flasher", and (c) a "methyl iodide-acetic acid splitter column". The carbonylation reactor is typically a stirred autoclave within which the reacting liquid contents are maintained automatically at a constant level. Into this reactor there are continuously introduced fresh methanol, sufficient water to maintain at least a finite concentration of water in the reaction medium, recycled catalyst solution from the flasher base, and recycled methyl iodide and methyl acetate from the overhead of the methyl iodide-acetic acid splitter column. Alternate distillation systems can be employed so long as they provide means for recovering the crude acetic acid and recycling to the reactor catalyst solution, methyl iodide, and methyl acetate. In the preferred process, carbon monoxide is continuously introduced into the carbonylation reactor just below the agitator which is used to stir the contents. The gaseous feed is, of course, thoroughly dispersed through the reacting liquid by this means. A gaseous purge stream is vented from the reactor to prevent buildup of gaseous by-products and to maintain a set carbon monoxide partial pressure at a given total reactor pressure. The temperature of the reactor is controlled automatically, and the carbon monoxide feed is introduced at a rate sufficient to maintain the desired total reactor pressure.

Liquid product is drawn off from the carbonylation reactor at a rate sufficient to maintain a constant level therein and is introduced to the flasher at a point intermediate between the top and bottom thereof. In the flasher, the catalyst solution is withdrawn as a base stream (predominantly acetic acid containing the rhodium and the iodide salt along with lesser quantities of methyl acetate, methyl iodide and water), while the overhead of the flasher comprises largely the product acetic acid along with methyl iodide, methyl acetate and water. A portion of the carbon monoxide along with gaseous by-products such as methane, hydrogen and carbon dioxide exits the top of the flasher.

The product acetic acid drawn from the base of the methyl iodide-acetic acid splitter column (it can also be withdrawn as a side stream near the base) is then drawn off for final purification such as to remove water as desired by methods which are obvious to those skilled in the art including, most preferably, distillation. The overhead from the methyl iodide-acetic acid splitter, comprising mainly methyl iodide and methyl acetate, is recycled to the carbonylation reactor along with fresh methyl iodide, the fresh methyl iodide being introduced at a rate sufficient to maintain in the carbonylation reactor the desired concentration of methyl iodide in the liquid reaction medium. The fresh methyl iodide is needed to compensate for losses of methyl iodide in the flasher and carbonylation reactor vent streams.

The crude dry acetic acid product is not adequately purified since it contains residual by-products such as organic and metal iodides, unsaturates, and carbonyl impurities of which crotonaldehyde, ethyl crotonaldehyde and 2-methyl-2-pentanal are the most prominent. In the high water carbonylation of methanol of Paulik et al (U.S. Pat. No. 3,769,329), which generally teaches that a substantial quantity of water helps in obtaining adequately high reaction rates, and in European patent application Ser. No. 0055618, which teaches that typically 14-15 wt. % water is in the reaction medium of a typical acetic acid plant using this technology, impurities such as 2-methyl-2-pentanal, crotonaldehyde and ethyl-crotonaldehyde are not present but become more of a problem as the water content is lowered in the low water carbonylation of methanol. Small amounts of these impurities degrade the commercial usefulness of the acetic acid product and, accordingly, it has been discovered that by treating the acetic acid with ozone and then contacting the acetic acid with activated carbon and/or an ion-exchange resin, it becomes possible to obtain a desired degree of purification as evidenced by the permanganate test.

According to the invention, the crude acetic acid is subject to ozonolysis by generating the ozone gas and bringing the gas into physical contact with the acetic acid product in the presence of a catalytically effective amount of an oxidation catalyst.

Ozone ($O_3$) is a gaseous allotropic form of oxygen in which three atoms form the molecule rather than the normal two. Although ozone is a strong oxidizing agent, it is not a specific oxidant and, hence, will oxidize any material it contacts which has a lower oxidation potential. As such, when it contacts the aforesaid impurities in acetic acid, it will oxidize the carbon to carbon double bond linkages of unsaturates, for example, which apparently contribute to short permanganate times in the acetic acid product. This theory of operation, however, is not to be regarded as essential to an understanding of the invention. Available data, as shown hereinafter, indicate that the benefit of the ozone contacting is due to the ability of the ozone to render iodides, unsaturates and carbonyl compounds inactive, thus preventing their influence on acetic acid either during storage or subsequent use.

Ozonolysis may be carried out by generating the ozone from any suitable source such as a quartz lamp, a silent electric discharge or spark discharge commonly called corona discharge, but it is preferable to obtain the ozone from a source of radiation in the range between about 1000 and 2950 angstrom units in wave length, applied in air or oxygen. For commercial production of ozone, it is preferable to use corona discharge technology on either air or oxygen. UV radiation type generators are usually only used on a small scale system. The maximum weight ratio of ozone in the liquid acetic acid is governed by the flammability limits of acetic acid — $O_2$ vapor phase compositions. In the examples hereinafter set forth, ozone was introduced into the mid point of a cylindrical vessel and contacted with a downwardly flowing stream of acetic acid at a temperature of about 95° F. (35° C.). Sufficient pressure was employed to keep the acetic acid below the flammability limit of 2.5 volume per cent in oxygen or 3.8 volume per cent in air (~10 psig in air or 25 psig in $O_2$).

The ozone exposure time will vary, but it has been found that the effect is substantially instantaneous, while on the other hand, over exposure is not harmful. Good results are obtained when the exposure time is less than one-half hour, usually about 1 to 15 minutes. The preferred quantity of ozone will range from about 3 ppm to 5000 ppm based on the weight of the acetic acid treated. High levels of ozone are not detrimental except for associated costs.

Ozonolysis may be carried out at temperatures of 70° F. (21° C.) to 115° F. (52° C.) in a continuous or batchwise fashion. Temperature and pressure considerations are not critical so long as flammability limits are not exceeded.

The iodides, unsaturates and carbonyl impurities in acetic acid apparently react with ozone to form a reactive oxygenated species or complex which may be separated from the acetic acid. Such separation can be accomplished by passing the solution through a carbonaceous material and/or a macroreticulated strong-acid cation exchange resin which is stable in the organic medium and has at least one per cent of its active sites converted to the silver or mercury ion-exchange form.

As indicated, the ion exchange resin has been at least partially converted to the silver or mercury form. It is important in practice to use an ion exchange resin with suitable properties. The ion exchange resin should not be of the gel-type. As is known, gel-type polymers are characterized by the fact that their porosity essentially depends on the volume increase which they exhibit upon exposure to a given solvent system. Ion exchange resins which depend essentially upon swelling for their porosity are not suitable for the practice of the present invention.

The ion exchange resins used in the present invention may thus be termed "non-gel-type" ion exchange resins. Such useful resins are typically considered to be macroreticular ion exchange resins and usually have pores considerably larger than those of the gel-type. However, the present invention is not limited to any specific pore-size of the ion-exchange resin. Usually the ion exchange resins used in the present invention have an average pore size from about 50 to 1,000 angstroms. Preferably, the average pore size is from about 200 to 700 angstroms.

The ion-exchange resin should also be of the type typically classified as a "strong acid" cation exchange resin. Preferably the resin of the "$RSO_3H$ type." It is beyond the scope of the present invention to teach how to manufacture or otherwise characterize ion exchange resins, as such knowledge is already well known in that art. For the purposes of the present invention it is sufficient to characterise an ion exchange resin useful therein as being a strongly-acidic cation exchange resin of the non-gel type, and thus macroreticulated.

A preferred ion exchange resin for use in the practice of the present invention is a macroreticulated resin comprised of a sulfonated copolymer of styrene and divinyl benzene. The most preferred resin such as that available from Rohm and Haas under the Amberlyst ® 15, has the following properties:

| Appearance | Hard, dry spherical particles |
| --- | --- |
| Typical particle size distribution percent retained on | |
| 16 mesh U.S. Standard Screens | 2-5 |
| −16 + 20 mesh U.S. Standard Screens | 20-30 |
| −20 + 30 mesh U.S. Standard Screens | 45-55 |
| −30 + 40 mesh U.S. Standard Screens | 15-25 |
| −40 + 50 mesh U.S. Standard Screens | 5-10 |
| Through 50 mesh, percent | 1.0 |
| Bulk density, lbs./cu.ft. | 38 (608 g/L) |
| Moisture, by weight | less than 1% |
| Percentage swelling from dry state to solvent-saturated state | |
| hexene | 10-15 |
| toluene | 10-15 |
| ethylene dichloride | 15-20 |
| ethyl acetate | 30-40 |
| ethyl alchohol (95%) | 60-70 |
| water | 60-70 |
| Hydrogen ion concentration meq./g.dry | 4.7 |
| Surface Area, $m^2/g$. | 50 |
| Porosity, ml.pore/ml.bead | 0.36 |
| Average Pore Diameter, Angstroms | 240 |

A final characteristic of the resin when used to remove iodide compounds from non-aqueous, organic media, and one that is inherent in most ion exchange resins meeting the foregoing requirements, especially when the resin is specifically indicated to be designated for non-aqueous applications, is that the resin is stable in the organic medium from which the iodide compounds are to be removed. By the term "stable," it is meant that the resin will not chemically decompose, or change more than about 50 percent of its dry physical dimension upon being exposed to the organic medium containing the iodide compounds.

The ion exchange resin as indicated above, should be at least partially converted to the silver or mercury form. Conversion to the silver form is preferred.

The method of converting the ion exchange resin to the silver or mercury form is not critical. Any mercury or silver salt which has reasonable solubility in water or a suitable non-aqueous organic medium can be used. Silver acetate and silver nitrate are typical salts. The organic medium which may be used to load silver ions on the exchange resin may be, for example, acetic acid. When mercury is desired, rather than silver, a suitable salt is mercuric acetate.

The ion exchange resin is converted, to the desired degree, to the silver or mercury form, by simply contacting the resin with a solution of the desired silver or mercury salt for a sufficient length of time to allow for association of the metal ions with the resin.

The amount of silver or mercury associated with the resin is not critical and may be from as low as about 1 percent of the active acid sites to as high as 100 percent, converted to the silver or mercury form. Preferably about 25 percent to about 75 percent are converted to the silver or mercury form, and most preferably about 50 percent. As stated previously, the preferred metal is silver.

As some silver may be leached from the silver-treated ion exchange resin during conditions of actual use, it may be useful to have a bed of ion-exchange resin which has not been previously converted to the silver-form, placed downstream of the bed of silver-treated ion exchange resin. With respect to the processing steps, the non-aqueous organic medium which contains the iodide impurities is simply placed in contact with the silver-loaded ion exchange resin described above, using any suitable means. For example, the resin may be packed into a column by pouring slurries thereof into a column. The organic medium is then simply allowed to flow therethrough. Any other suitable means of placing the resin in contact with the organic medium may be employed.

When a packed column is used, the organic medium is usually allowed to flow therethrough at a predetermined rate. The particular rate used in any given instance will vary depending upon the properties of the organic medium, the particular resin, the degree and nature of the iodide compounds to be removed, and the percent of iodide compounds to be removed.

A typical flow rate, such as is used when acetic acid is to be purified, is from about 0.5 to about 20 bed volumes per hour ("BV/hr"). A bed volume is simply the volume of the resin bed. A flow rate of 1 BV/hr then means that a quantity of organic medium equal to the volume occupied by the resin bed passes through the resin bed in a one hour time period. Preferred flow rates are usually about 6 to about 10 BV/hr and the most preferred flow rate is usually about 8 BV/hr.

The temperature at which the iodide compound removal takes place is also not critical. Broadly, the method may be performed at any temperature from about the freezing point of the organic liquid to the decomposition temperature of the resin. As a practical matter, the temperature employed is usually from about 17° C. to about 100° C., typically from about 18° C. to about 50° C., and preferably under ambient conditions of about 20° C. to about 45° C.

In one embodiment of the present invention the non-aqueous organic medium is contacted with a carbonaceous material in addition to contacting the aforementioned ion exchange resin. Preferably, the carbonaceous material is used in a contacting step prior to the step of contacting the ion exchange resin. Although the aforementioned ion exchange resin is useful in removing iodide compounds, it is not very effective in removing iodine itself.

As discussed in U.S Pat. No. 1,843,354, carbonaceous materials have been found to be effective absorbers of iodine. Carbonaceous materials listed therein include activated carbons, wood charcoals, bone char, lignite and the like. Preferably, activated carbon is used. It appears that activated carbons of the type usually identified as gas-phase carbons work best in removing iodine from such organics. Gas-phase activated carbons typically have surface areas on the order of 1,000 to 2,000 $m^2/g$. The most preferred activated carbon is one derived from coconut shells, such as is available under the designation Pittsburgh PCB 12×30 carbon.

Usually the non-aqueous organic medium is placed in contact with the carbonaceous material in the same manner as with the ion exchange resin, under the same or comparable conditions.

The present invention can be more fully understood by referring to the following examples which illustrate the best mode now contemplated for carrying out of the invention. In the examples the "permanganate time" is determined as follows:

One ml of an aqueous 0.1N potassium permanganate solution is added to 50 ml of acetic acid in a graduated cylinder at room temperature. The cylinder is stoppered and shaken, and a timer is immediately started to measure the time required for the purple color to change to a yellow-amber end point which is compared to a standard reference color indicating the content of unsaturate, iodide and carbonyl impurities.

EXAMPLE 1

185 grams of glacial finished acetic acid (obtained from a low water carbonylation of methanol to acetic acid employing a halogen promoted rhodium catalyst) spiked to contain 231 ppm crotonaldehyde and 224 ppm ethyl crotonaldehyde impurities and having a permanganate time of 0.1 minutes were treated for 30 minutes with ozone made from air (0.5 vol. % ozone in air).

EXAMPLE 2

Unspiked glacial finished acetic acid was treated with ozone in the manner of Example 1 in which the contact time with ozone was 10 and 19 minutes.

EXAMPLE 3

Glacial finished acetic acid was spiked with ethyl crotonaldehyde (23.2 ppm) and treated with ozone in the manner of Example 1.

EXAMPLE 4

A glacial finished acetic acid overhead cut identified as T-840H was treated with ozone and comprised to an untreated sample.

EXAMPLE 5

Two samples of glacial acetic acid, identified as V-783 outlet, were treated with ozone at different contact times of 1 and 3 minutes and compared to an untreated sample.

EXAMPLE 6

A sample of the untreated glacial acetic acid used in Example 5 was treated with ozone in the presence of 0.5 wt. % manganese dioxide catalyst in two different runs and compared to a sample that was treated with ozone in the absence of a catalyst and a sample that was treated with 0.5% manganese dioxide and air.

The test results of Examples 1 to 6 and the parameters of the tests are set forth below in Table 1.

EXAMPLE 7 to 12

In the following examples, improvement in permanganate time is further achieved by ozonolysis followed by activated carbon treatment. A one-half gallon sample of ozone treated acetic acid, as obtained in Example 1, was passed through activated carbon in a flooded or trickle bed system at ambient room temperature and pressure. The results are shown in Table 2 below.

TABLE 2

| Example | Permanganate Time, Min |
|---|---|
| 7. untreated glacial acetic acid | 0.25 |
| 8. ozone treated acid | 1.5 |
| 9. ozone treated acid & activated carbon* (Flooded Bed) | 2.5 |
| 10. ozone treated acid & activated carbon* (Trickle Bed) | 4.5 |
| 11. ozone treated acid & activated carbon* (Flooded contactor) | 2.0 |
| 12. ozone treated acid & activated carbon** (Trickle Bed) | 10.0 |

*Calgon F300
**Cocoanut Charcoal

What is claimed:

1. A method for improving the permanganate time of acetic acid produced by the low water carbonylation of methanol in a reaction medium comprising methanol, carbon monoxide, from 0.5 to 30 wt. % methyl acetate, from 5 to 20 wt. % methyl iodide, from 2 to 20 wt. % soluble alkali metal iodide, and a halogen-promoted rhodium catalyst in the presence of less than 14 wt. % water which comprises contacting said acid with ozone and thereafter contacting the acetic acid with activated carbon to provide an acetic acid product having an improved permanganate time.

2. The method of claim 1 wherein the quantity of ozone contacted is greater than about 3 ppm based on the weight of acetic acid tested.

3. The method of claim 1 wherein the acetic acid product is further contacted with an ion-exchange resin which has been at least partially converted to the silver or mercury form for removal of alkyl iodides.

4. The method of claim 3 wherein the alkyl iodide is selected from the group consisting of methyl iodide, hexyl iodide and mixtures thereof.

* * * * *

TABLE 1

| Ex. | HAC | Crot. Cont. (ppm) | Et Crot. Cont. (ppm) | $KMnO_4$ Time (min.) | Peroxide Concen. (ppm) | $O_3$ Contact Time (min.) | Feed $O_3$ Concen. Based. on HAC (ppm) | $O_3$ Concen. in air (%) | $O_3$ Gener. Rate (mg/min.) | Total Gas Cont. ( ) | Total $O_3$ Cont. (mg) | Wt. of HAC Treated (gm) |
|---|---|---|---|---|---|---|---|---|---|---|---|---|
| 1 | Spiked HAC blank* | 231 | 224 | 0.1 | — | — | — | — | — | — | — | 185.0 |
|   | Spiked HAC + $O_3$* | 9 | 3 | 0.25 | — | 30 | — | — | — | — | — | 185.0 |
| 2 | HAC blank | 5.2 | 5.0 | 1.5 | — | — | 0 | — | — | 0 | 0 | 183.2 |
|   | HAC + $O_3$ (10 min.) | 0.1 | 0.6 | — | — | 10 | 42 | 0.09 | 0.77 | 4.0 | 7.7 | 183.2 |
|   | HAC + $O_3$ (19 min.) | 0.1 | 0.5 | 5.0 | <3 | 19 | 88 | 0.09 | 0.82 | 8.1 | 15.6 | 177.9 |
| 3 | Spiked HAC** | 6.2 | 23.2 | 0.25 | — | — | 0 | — | — | 0 | 0 | 198.9 |
|   | Spiked 2 min $O_3$ | 0.1 | 0.1 | — | — | 2 | 56 | 0.6 | 5.5 | 0.86 | 11.1 | 198.9 |
|   | Spiked 4 min $O_3$ | 0.1 | 0.5 | — | — | 4 | 114 | 0.6 | 5.5 | 1.72 | 22.1 | 193.7 |
|   | Spiked 5 min $O_3$ | 0.1 | 0.3 | 1.0 | <3 | 5 | 146 | 0.6 | 5.5 | 2.15 | 27.6 | 188.4 |
| 4 | T-8404H blank | 6.4 | 5.2 | 1.0 | — | — | — | — | — | — | — | — |
|   | T-8404H + $O_3$ | 0.1 | 0.1 | 8 | — | 1.0 | 22 | 0.60 | 4.1 | 0.32 | 4.1 | 190.0 |
| 5 | V-783 blank | 6.2 | 7.1 | 0.75 | — | — | — | — | — | — | — | — |
|   | V-783 + $O_3$ | .1 | .1 | 3 | — | 1.0 | 34 | 0.4 | 6.2 | 0.73 | 6.2 | 182.22 |
|   | V-783 + $O_3$ | .1 | .1 | 3 | — | 3.0 | 26 | 0.1 | 1.6 | 2.05 | 4.9 | 191.22 |
| 6 | V-783 + $O_3$ + $MnO_2$ | .1 | .1 | 4 | — | 1.0 | 6 | .07 | 1.1 | 0.74 | 1.1 | 188.91 |
|   | V-783 + $O_3$ | .1 | .1 | 3.25 | — | 6 | 36 | .05 | 1.1 | 2.5 | 6.8 | 190.21 |
|   | V-783 + $O_3$ + $MnO_2$ | .1 | .1 | 12 | — | 6 | 36 | .05 | 1.1 | 2.5 | 6.8 | 187.60 |
|   | V-783 + air + $MnO_2$ | 6.0 | 7.3 | 0.75 | — | — | — | 0 | 0 | 2.5 | 0 | 185.0 |

*Spiked with Crotonaldehyde and Ethyl Crotonaldehyde
**Spiked with Ethyl Crotonaldehyde